United States Patent
Sasaki

(10) Patent No.: US 8,451,533 B2
(45) Date of Patent: May 28, 2013

(54) FLUORESCENCE MICROSCOPE

(75) Inventor: Yutaka Sasaki, Yokohama (JP)

(73) Assignee: Nikon Corporation, Tokyo (JP)

( * ) Notice: Subject to any disclaimer, the term of this patent is extended or adjusted under 35 U.S.C. 154(b) by 9 days.

(21) Appl. No.: 12/801,222

(22) Filed: May 27, 2010

(65) Prior Publication Data
US 2011/0043907 A1    Feb. 24, 2011

Related U.S. Application Data

(63) Continuation of application No. PCT/JP2007/071485, filed on Nov. 19, 2008.

(30) Foreign Application Priority Data

Nov. 27, 2007 (JP) ................................ 2007-306167

(51) Int. Cl.
*G02B 21/00* (2006.01)

(52) U.S. Cl.
USPC .......................................... 359/368; 359/380

(58) Field of Classification Search
USPC ................................................. 359/368–390
See application file for complete search history.

(56) References Cited

U.S. PATENT DOCUMENTS

| | | | | |
|---|---|---|---|---|
| 5,434,954 A | * | 7/1995 | Kawauchi et al. | 345/440 |
| 5,754,571 A | * | 5/1998 | Endoh et al. | 372/20 |
| 6,075,643 A | | 6/2000 | Nonoda et al. | |
| 6,192,267 B1 | * | 2/2001 | Scherninski et al. | 600/473 |
| 6,262,837 B1 | * | 7/2001 | Nagano et al. | 359/368 |
| 6,909,542 B2 | * | 6/2005 | Sasaki | 359/385 |
| RE38,847 E | | 10/2005 | Nonoda et al. | |
| 2005/0179892 A1 | * | 8/2005 | Gerstner et al. | 356/318 |
| 2006/0253036 A1 | * | 11/2006 | Takeuchi et al. | 600/478 |
| 2008/0151367 A1 | * | 6/2008 | Aizaki et al. | 359/389 |

FOREIGN PATENT DOCUMENTS

| | | |
|---|---|---|
| JP | 11-223773 | 8/1999 |
| JP | 2002-014043 | 1/2002 |
| JP | 2004-258547 | 9/2004 |
| JP | 2005-331889 | 12/2005 |

OTHER PUBLICATIONS

Second and Supplementary Notice (Form PCT/IB/308).
Notification of Transmittal of Translation of the International Preliminary Report on Patentability (Form PCT/IB/338 & 373).
Translation of Written Opinion of the International Searching Authority (Form PCT/ISA/237).

* cited by examiner

*Primary Examiner* — Thong Nguyen

(57) ABSTRACT

A fluorescence microscope 100 includes an illumination optical system 120 that illuminates a sample with excitation light, fluorescence detection optical systems 130, 140 and 150 that detect fluorescence from the sample, optical members 8, 12, 13, 16, 17 and 20 that are disposed on an optical path of the illumination optical system and on an optical path of the fluorescence detection optical system, have different wavelength characteristics with each other, and are included in the illumination optical system and in the fluorescence detection optical system, a memory 23 that stores the wavelength characteristic of each of the optical members, and a display 23*a* that displays each of the wavelength characteristic read out from the memory on the same frame, and displays fluorescence detection wavelength range of a detectable fluorescent dye added to the sample.

7 Claims, 8 Drawing Sheets

MONITOR SCREEN

FLUORESCENCE MICROSCOPE

The present application is a continuation application based on International Application PCT7JP2008/0714B5, filed Nov. 19, 2008, and foreign priority benefit is based upon Japanese Patent Application 2007-306167, filed Nov. 27, 2007, the entire contents thereof being incorporated herein by reference.

TECHNICAL FIELD

The present invention relates to a fluorescence microscope having a display capable of showing wavelength characteristic.

BACKGROUND ART

In a fluorescence microscope, optical elements having wavelength characteristics such as an excitation filter, an absorption filter, a barrier filter, a dichroic filter, and the like have been disposed on the optical path so as to detect desired fluorescence by means of a detection device to display on a display such as a monitor to be observed by an observer (for example, see Japanese Patent Application Laid-Open No. 11-223773).

However, in a conventional fluorescence microscope, wavelength characteristics of optical elements such as an excitation filter, an absorption filter, a barrier filter, a dichroic filter, and the like, which are disposed on the optical path for detecting desired fluorescence, and wavelength characteristics of desired fluorescence have been only given separately by a catalog with specifications tables. Accordingly, a user cannot tell which wavelength range is the wavelength characteristics of the fluorescence image obtained by the fluorescence microscope, or the user cannot visually know in advance whether a fluorescence image of desired wavelength range can be obtained, so that it has been a problem.

DISCLOSURE OF THE INVENTION

The present invention is made in view of the aforementioned problems, and has an object to provide a fluorescence microscope capable of visually recognizing in advance whether a fluorescence image of desired wavelength range can be obtained, by means of wavelength characteristics of optical elements such as lenses, filters and beam splitters disposed on the optical path of the optical system and wavelength characteristic of fluorescent dye.

In order to solve the problems, the present invention provides a fluorescence microscope comprising: an illumination optical system that illuminates a sample with excitation light; a fluorescence detection optical system that detects fluorescence from the sample; optical members that are disposed on an optical path of the illumination optical system and on an optical path of the fluorescence detection optical system, have different wavelength characteristics with each other, and are included in the illumination optical system and in the fluorescence detection optical system; a memory that stores the wavelength characteristic of each of the optical members; and a display that displays each of the wavelength characteristics read out from the memory on the same frame, and displays fluorescence detection wavelength range of a detectable fluorescent dye added to the sample.

The present invention makes it possible to provide a fluorescence microscope capable of visually recognizing in advance whether a fluorescence image of desired wavelength range can be obtained, by means of wavelength characteristics of optical elements such as lenses, filters and beam splitters disposed on the optical path of the optical system and wavelength characteristic of fluorescent dye.

EMBODIMENT FOR CARRYING OUT THE INVENTION

An embodiment of the present invention is explained with reference to accompanying drawings. Incidentally, the following embodiment is only for better understanding of the present invention, so that there is no intention of rejecting operable addition or substitution made by a person having ordinary skill in the art within a scope of technical thought of the present invention.

Figure 1:
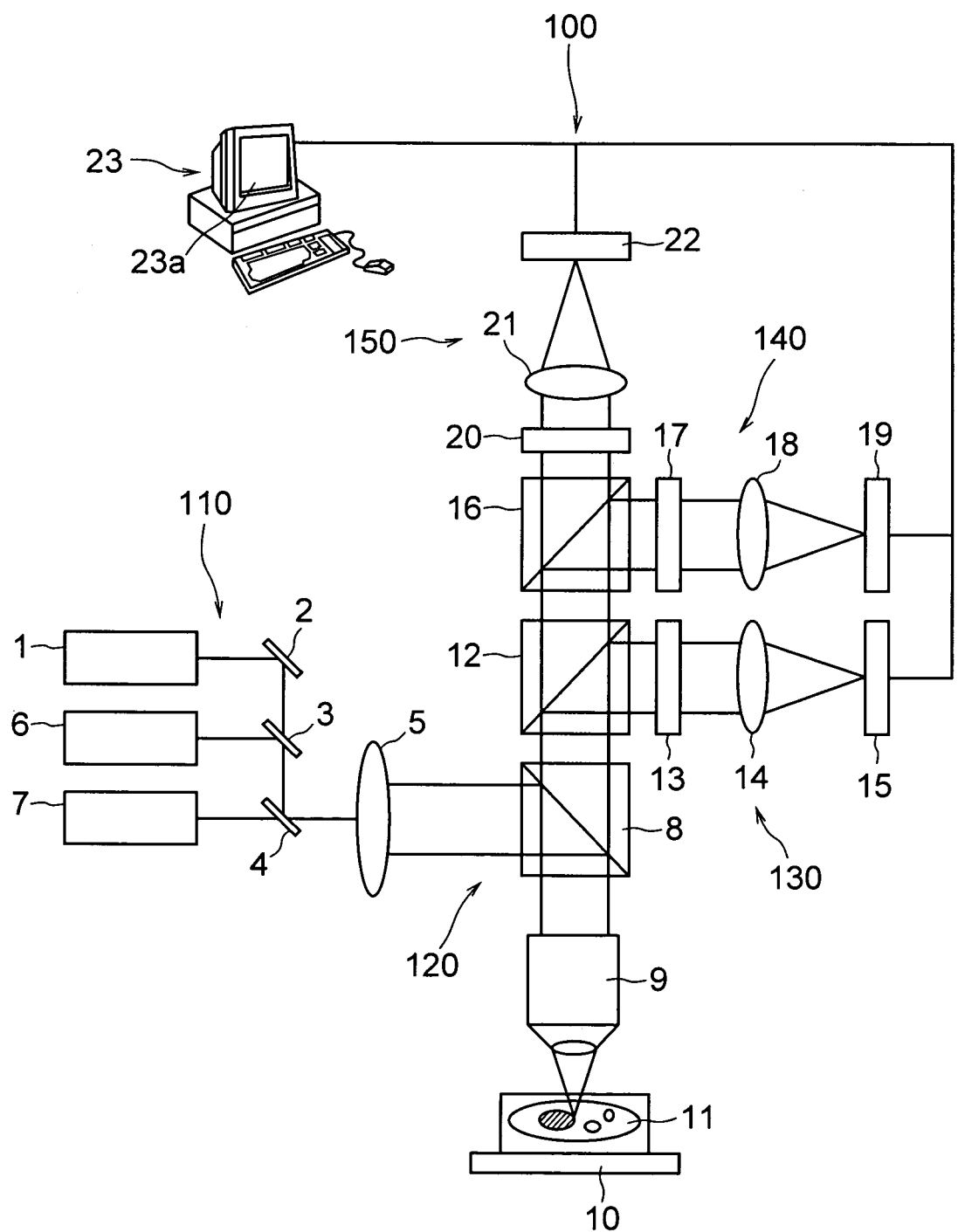
FIG. 1 is a schematic diagram showing a fluorescence microscope according to an embodiment.
Figure 2:
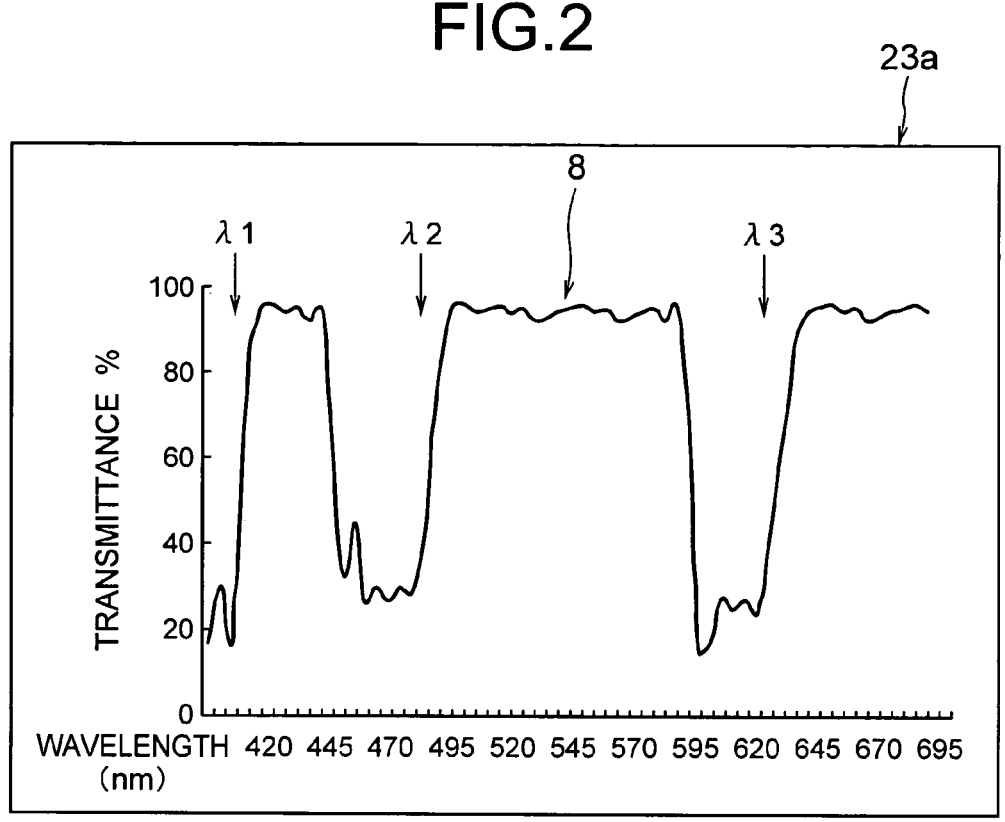
FIG. 2 is a graph showing an example of spectral transmittance of an excitation dichroic mirror.
Figure 3:
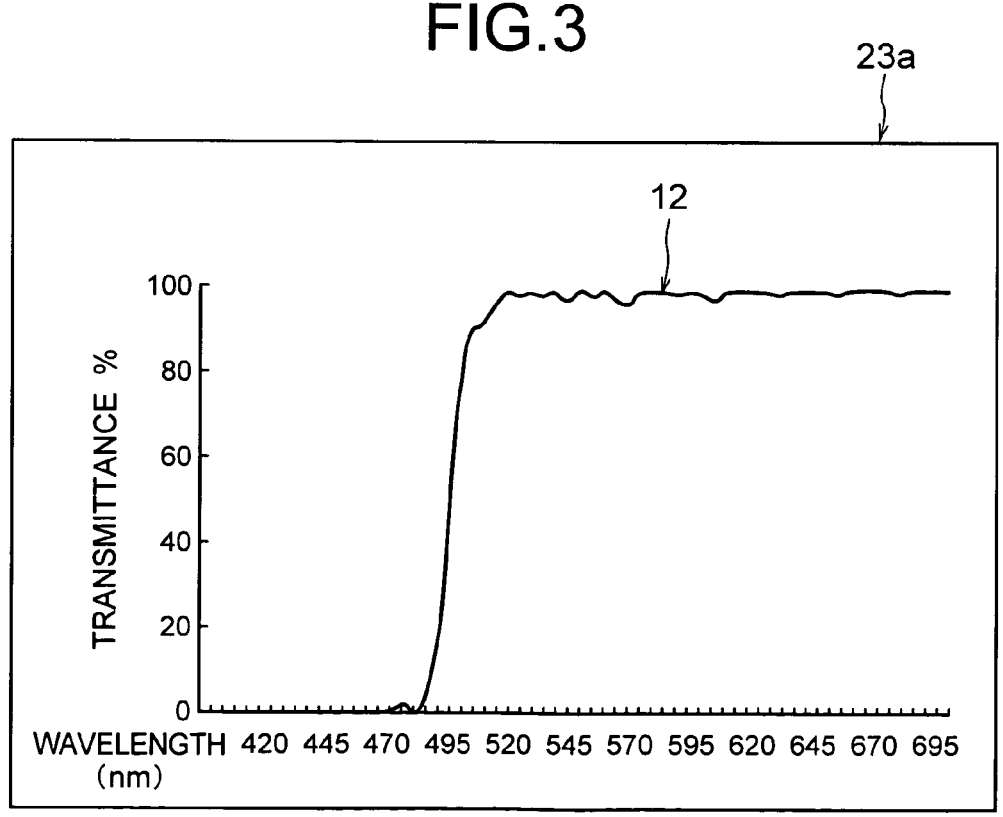
FIG. 3 is a graph showing an example of spectral transmittance of a first dichroic mirror.
Figure 4:
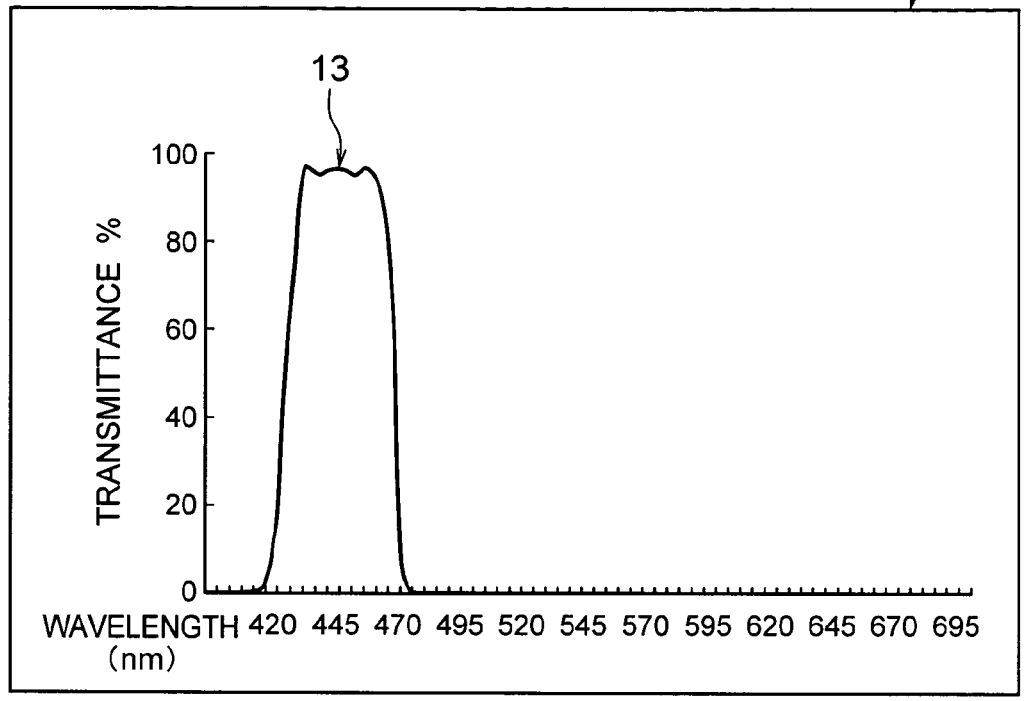
FIG. 4 is a graph showing an example of spectral transmittance of a first absorption filter.
Figure 5:
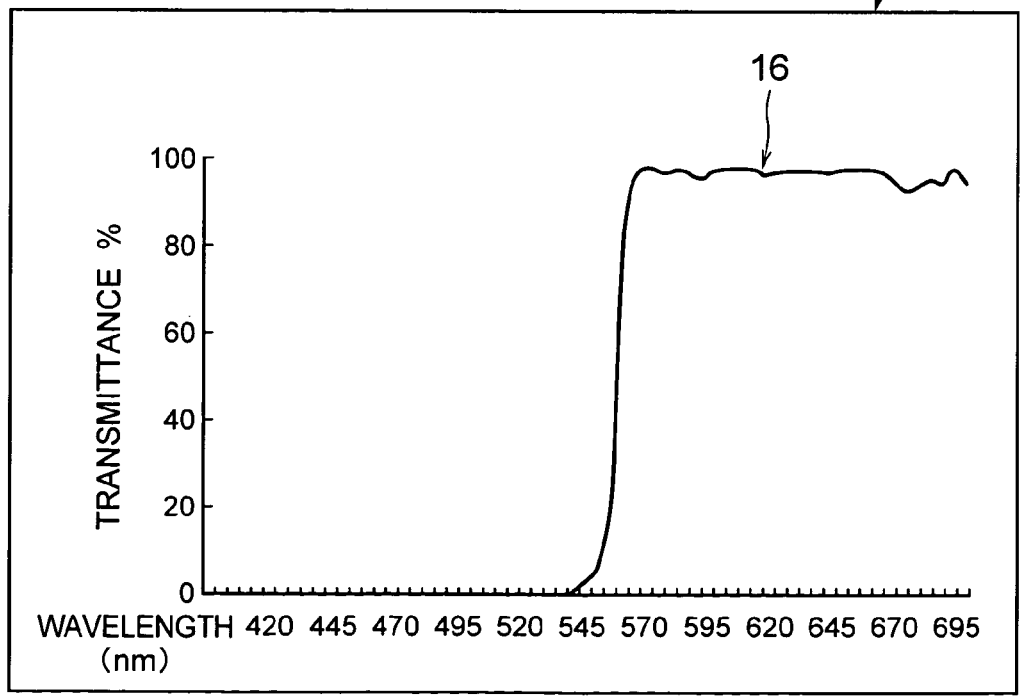
FIG. 5 is a graph showing an example of spectral transmittance of a second dichroic mirror.
Figure 6:
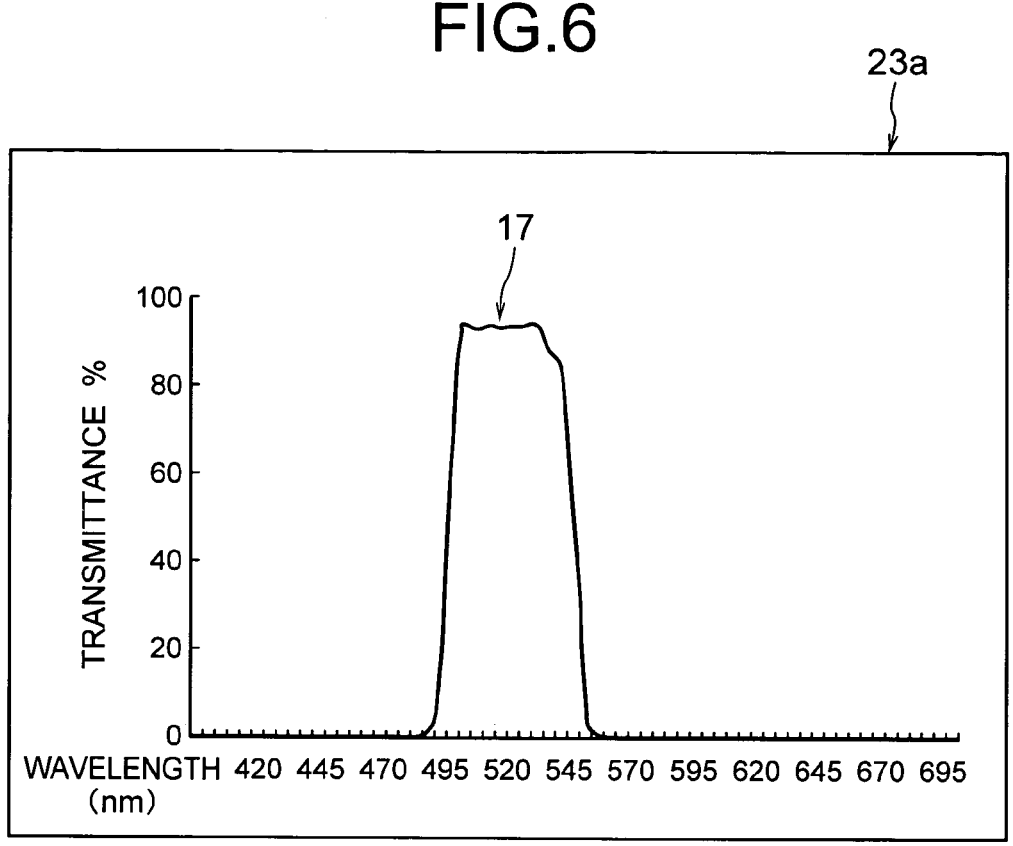
FIG. 6 is a graph showing an example of spectral transmittance of a second absorption filter.
Figure 7:
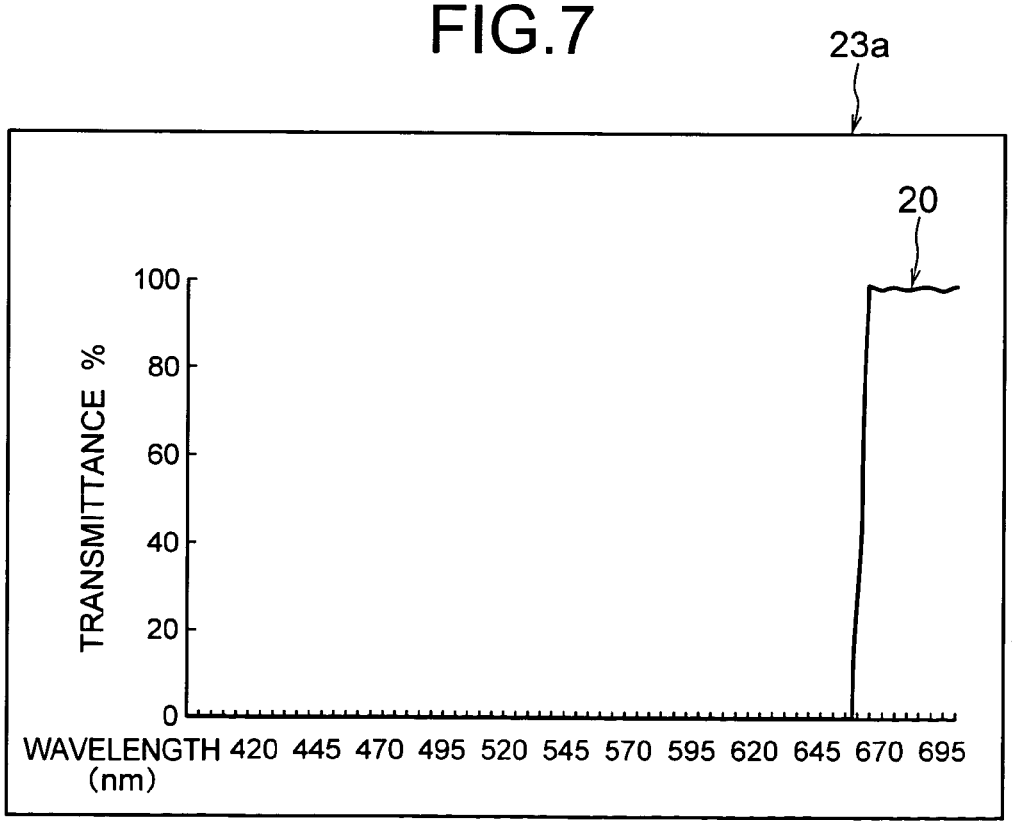
FIG. 7 is a graph showing an example of spectral transmittance of a third absorption filter.
Figure 8:
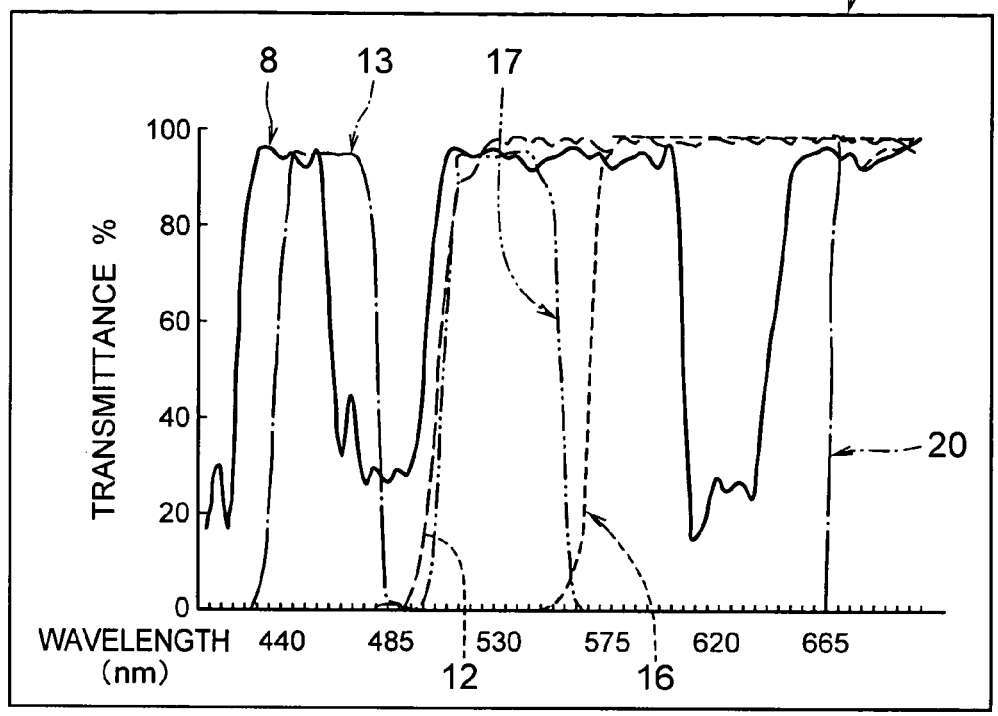
FIG. 8 is a graph showing an example of spectral transmittance of a dichroic mirror and an absorption filter disposed on the optical path in a superposing manner.
Figure 9:
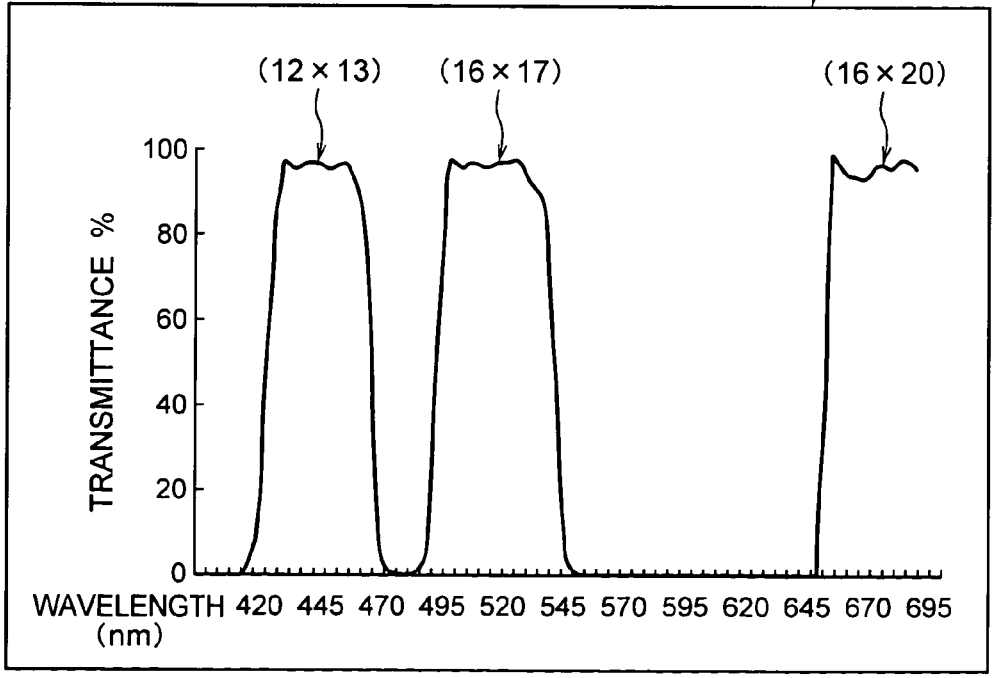
FIG. 9 is a graph showing an example of combined spectral transmittance of a dichroic mirror and an absorption filter.
Figure 10:
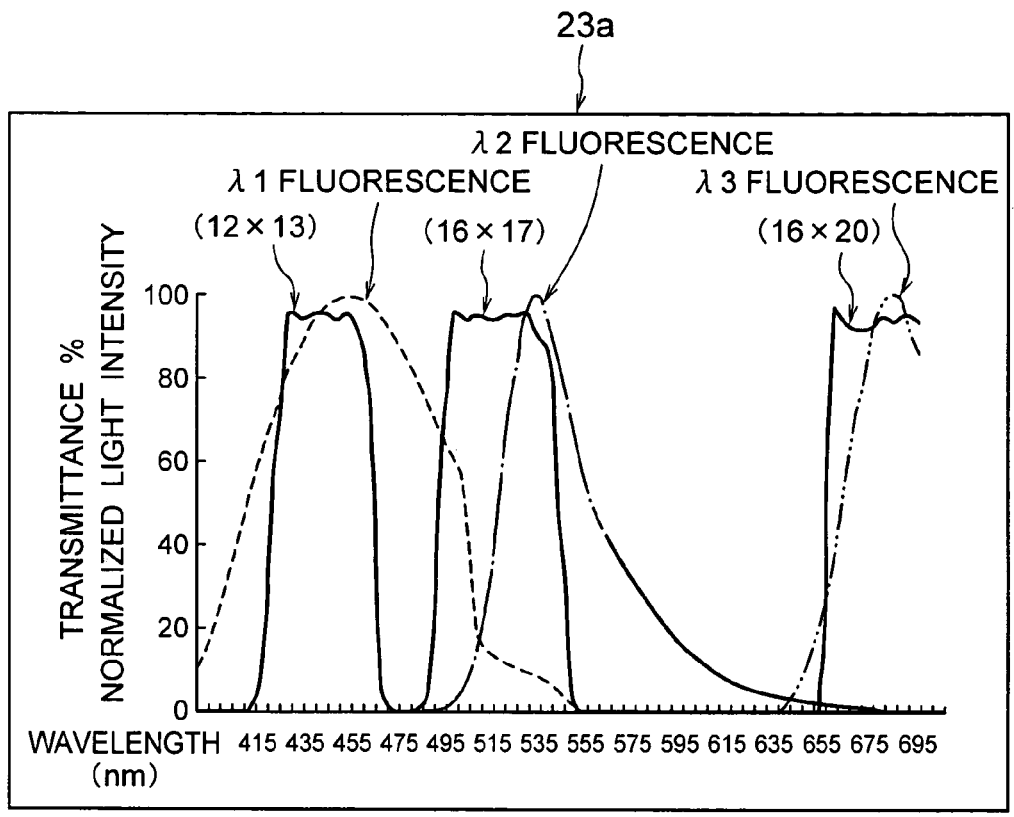
FIG. 10 is a graph showing an example of combined spectral transmittance and luminescence property of the fluorescence dye in a superposing manner.

FIG. 1 is a schematic diagram showing a fluorescence microscope according to an embodiment. FIG. 2 is a graph showing an example of spectral transmittance of an excitation dichroic mirror. FIG. 3 is a graph showing an example of spectral transmittance of a first dichroic mirror. FIG. 4 is a graph showing an example of spectral transmittance of a first absorption filter. FIG. 5 is a graph showing an example of spectral transmittance of a second dichroic mirror. FIG. 6 is a graph showing an example of spectral transmittance of a second absorption filter. FIG. 7 is a graph showing an example of spectral transmittance of a third absorption filter. FIG. 8 is a graph showing an example of spectral transmittance of a dichroic mirror and an absorption filter disposed on the optical path in a superposing manner. FIG. 9 is a graph showing an example of combined spectral transmittance of a dichroic mirror and an absorption filter. FIG. 10 is a graph showing an example of combined spectral transmittance and luminescence property of the fluorescence dye in a superposing manner.

In FIG. 1, laser light (for example, wavelength $\lambda 1 = 408$ nm) emitted from an excitation laser light source 1 is reflected by a mirror 2 toward a dichroic mirror 3, transmits through the dichroic mirror 3, and is reflected by a dichroic mirror 4 toward an expander lens 5. Laser light (for example, wavelength λ2=488 nm) emitted from an excitation laser light source 6 is reflected by the dichroic mirror 3 toward the dichroic mirror 4, and reflected by the dichroic mirror 4 toward the expander lens 5. Laser light (for example, wavelength λ3=633 nm) emitted from an excitation laser light source 7 transmits through the dichroic mirror 4, and is incident on the expander lens 5. Respective laser light emitted from three excitation laser light sources 1, 6 and 7 is combined and incident on the expander lens 5. In this manner, the excitation laser light source device 110 is constructed. Incidentally, the number of excitation laser light source is not limited to three, and any other number can suitably be used.

Combined laser light expanded and substantially collimated by the expander lens 5 is incident on an excitation dichroic mirror 8, reflected toward an objective lens 9, and converged by the objective lens 9 onto a sample 11 placed on a stage 10. The excitation dichroic mirror 8 has spectral transmittance 8 (the same reference number as the optical member is attached for the explanation. The same is applied to the others) shown in FIG. 2, reflects laser light having wavelengths λ1, λ2 and λ3, and illuminates the sample 11. In FIG. 2, vertical axis shows transmittance (unit: %) and horizontal axis shows wavelength (unit: nm), the same is applied to the following graphs, and the explanations are omitted in the following graphs.

As shown in FIG. 1, fluorescence excited by excitation laser light incident on the sample 11 is converged by the objective lens 9, transmits through the excitation dichroic mirror 8, and is incident on a first dichroic mirror 12. Combined laser light reflected by the sample 11 is reflected by the excitation dichroic mirror 8 toward the expander lens 5. An illumination optical system 120 is constructed from the expander lens 5 to the objective lens 9.

The first dichroic mirror 12 has spectral transmittance 12 shown in FIG. 3, reflects light having wavelength of substantially 490 nm or less toward a first absorption filter 13, and transmits light having wavelength exceeding thereof. The first absorption filter 13 has spectral transmittance 13 shown in FIG. 4, transmits light having wavelength from about 420 nm to about 470 nm, and reflects light exceeding the range. As shown in FIG. 1, light transmitted through the first absorption filter 13 is converged by a converging lens 14, and light intensity thereof is detected by a first photomultiplier (hereinafter abbreviated as PMT) 15.

A first detection optical system 130 is constructed from the objective lens 9 to the PMT 15. In this manner, the first detection optical system 130 detects the first fluorescence emanated from the sample 11 excited with excitation laser light having wavelength of λ1 (408 nm).

A plurality of first dichroic mirrors 12, whose wavelength characteristics are different with each other, are provided on an unillustrated electric turret so as to be exchangeably provided on the optical path, a detecting device such as a photocoupler or electric switch for detecting the first dichroic mirror 12 disposed on the optical path upon rotating the turret is provided, and a controller 23 constructed by, for example, a personal computer and the like (hereinafter simply called as a PC) controls rotation of the turret and detects the first dichroic mirror.

As shown in FIG. 1, light transmitted through the first dichroic mirror 12 is incident on a second dichroic mirror 16. The second dichroic mirror 16 has spectral transmittance 16 shown in FIG. 5, reflects light having wavelength about 550 nm or less toward a second absorption filter 17, and transmits light having wavelength exceeding thereof. The second absorption filter 17 has spectral transmittance 17 shown in FIG. 6, transmits light having wavelength from about 495 nm to about 550 nm, and reflects light having wavelength exceeding the range. As shown in FIG. 1, light transmitted through the second absorption filter 17 is converged by a converging lens 18, and detected by a second PMT 19. A second detection optical system 140 is constructed from the objective lens 9 to the PMT 19. In this manner, the second detection optical system 140 detects the second fluorescence emanated from the sample 11 excited with excitation laser light having wavelength of λ2 (488 nm).

Similar to the first dichroic mirror 12, a plurality of second dichroic mirrors 16, whose wavelength characteristics are different with each other, are provided on an unillustrated turret so as to be exchangeably provided on the optical path, a detecting device such as a photocoupler or electric switch for detecting the second dichroic mirror 16 disposed on the optical path upon rotating the turret is provided, and the PC 23 controls rotation of the turret and detects the second dichroic mirror 16.

As shown in FIG. 1, light transmitted through the second dichroic mirror 16 is incident on a third absorption filter 20. The third absorption filter 20 has spectral transmittance 20 shown in FIG. 7, transmits light having wavelength exceeding about 650 nm, and reflects light having wavelength less than this. As shown in FIG. 1, light transmitted through the third absorption filter 20 is converged by a converging lens 21, and detected by a third PMT 22. A third detection optical system 150 is constructed from the objective lens 9 to the PMT 22. In this manner, the third detection optical system 150 detects the third fluorescence emanated from the sample 11 excited with excitation laser light having wavelength of λ3 (633 nm).

Fluorescence signal detected by each PMT 15, 19, 22 is sent to the PC 23, carried out image processing by the PC 23, and displayed on the monitor 23a. In this manner, the fluorescence microscope 100 according to the present embodiment is constructed.

In the above-described explanation, the illumination optical system 120, the first detection optical system 130, the second detection optical system 140, and the third detection optical system 150 are constructed with using a portion of the optical system in common.

In the fluorescence microscope 100 according to the present embodiment, spectral transmittance regarding each of dichroic mirrors 8, 12 and 16 shown in FIG. 2, 3 or 5, and each of absorption filters 13, 17 and 20 shown in FIG. 4, 6 or 7 is stored in a memory of the PC 23, and spectral transmittance of the dichroic mirror and the absorption filter disposed on the optical path can be shown on the monitor 23a, which is a display, of the PC 23. Here, the PC 23 works as a display for showing spectral transmittance.

As shown in FIG. 8, with displaying transmitting wavelength range on the monitor 23a by superposing spectral transmittance of dichroic mirrors 8, 12 and 16, and absorption filters 13, 17 and 20 disposed on the optical path, the user can visually confirm wavelength range capable of being detected by the PMT 15, 19 and 22.

As shown in FIG. 9, the PC 23 can display combined result multiplying each spectral transmittance by the calculation means on the monitor 23a, so that transmitting wavelength range can visually be confirmed. FIG. 9 shows combined result by multiplying each spectral transmittance shown in FIG. 8. In FIG. 9, (12×13) shows spectral transmittance multiplying spectral transmittance of the first dichroic mirror 12 by that of the first absorption filter 13, (16×17) shows spectral transmittance multiplying spectral transmittance of the second dichroic mirror 16 by that of the second absorption filter 17, and (16×20) shows spectral transmittance multiplying spectral transmittance of the second dichroic mirror 16 by that of the third absorption filter 20. In this manner, with combining each spectral transmittance, the graph becomes single line, so that the user can visually judge whether the dichroic mirror and the absorption filter correspond to the fluorescent dye to be detected, or whether it can actually be obtained as a fluorescence image.

Since the PC 23 has a memory in which fluorescence characteristics of various fluorescent dyes are stored, with inputting fluorescence wavelength characteristics of the fluorescent dye, which is added to the sample 11 by the user, into the memory of the PC 23, λ1 fluorescence, λ2 fluorescence and λ3 fluorescence of the added fluorescent dye are displayed on the monitor 23a together with combined spectral transmittance (13×13) [sic], (16×17) and (16×20) of various optical members on the fluorescence microscope 100 side in superposing manner as shown in FIG. 10.

The calculation means of the PC 23 compares fluorescence wavelength of the added fluorescent dye with combined spectral transmittance on the fluorescence microscope 100 side, and when the fluorescence wavelength of the fluorescent dye cannot be detected, the monitor 23a displays a warning display that notifies which fluorescence wavelength cannot be detected to the user. As a warning display displayed on the monitor 23a, for example, combination of optical members and wavelength characteristics thereof suitable for detecting the fluorescent dye that is displayed to be unable to be detected under the present condition are specifically informed.

Here, with normalizing the maximum light intensity as 100(%), fluorescence wavelength characteristics of the fluorescent dye becomes possible to display together with combined spectral transmittance in a superposing manner. Accordingly, relation between combined spectral transmittance combined each optical member (12×13), (16×17), (16×20) shown by the solid line in FIG. 10 and fluorescence wavelength characteristics of each wavelength λ1, λ2, λ3 can visually be confirmed. As a result, whether desired fluorescence can be detected or not can be confirmed before illuminating the sample 11 with excitation laser light 1, 6, and 7, so that fluorescence detection failure can be prevented.

Figure 11:
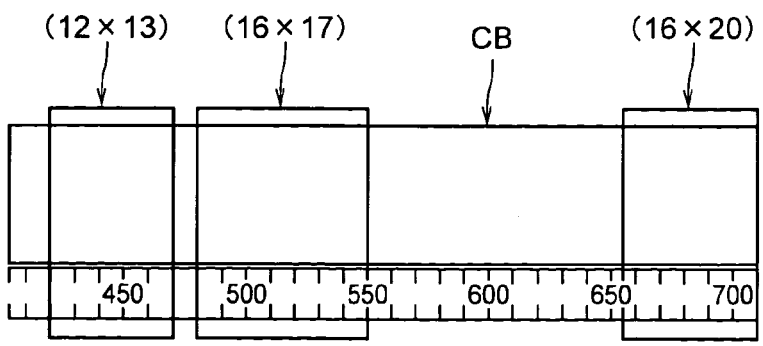
FIG. 11 is a graph showing an example of combined spectral transmittance range of each optical element together with a color bar.

As shown in FIG. 11, the display (monitor 23a) can be confirmed more visually by displaying combined spectral transmittance range of each optical member (12×13), (16×17), (16×20) together with a color bar CB in a frame display. Although combined spectral transmittance range can be confirmed more visually by the frame display, the range may be confirmed by, for example, a shading of color instead of the frame display.

In the above explanation, although three dichroic mirrors, three absorption filters, and three fluorescent dyes (three excitation lasers) are explained, combination of dichroic mirrors, absorption filters, and fluorescent dyes are not limited to this, and with automatically or manually designating wavelength characteristics of dichroic mirrors, absorption filters and fluorescent dyes, wavelength range of detectable fluorescence can be confirmed in advance.

Moreover, the PC 23 stores spectral transmittance of not only dichroic mirrors and absorption filters, but also optical members of the fluorescence microscope 100 such as, for example, an expander lens, a condenser lens, excitation filters, an objective lens, converging lenses, and the like and spectral sensitivity of detectors in the memory, and with combining and displaying on the monitor 23a as described above, the user can further precisely set and select optical members corresponding to fluorescent dye to be used and can confirm in advance whether fluorescence from fluorescent dye can be detected in the optical system to be used.

(Variation)

Figure 12:
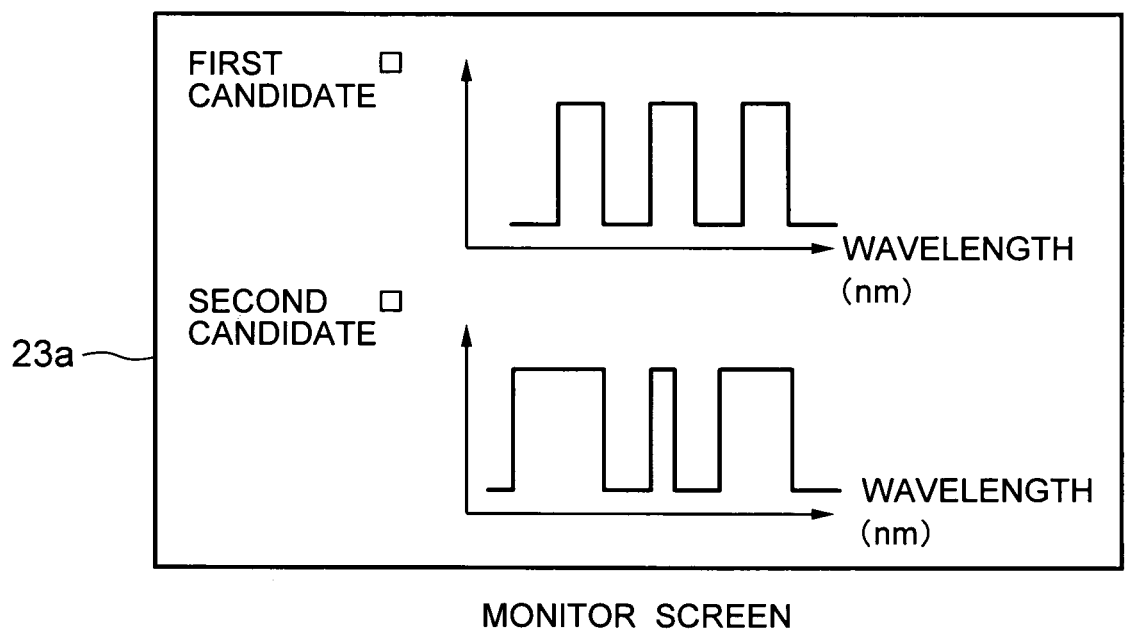
FIG. 12 is a view showing an example of a monitor frame according to a variation of the embodiment.

Then, a Variation of the Present Embodiment is explained. FIG. 12 shows an example of a monitor frame according to a variation of the present embodiment.

In the variation according to the present embodiment shown in FIG. 12, candidates of fluorescence detection wavelength range by the combination of various filters and dichroic mirrors set by the user are shown on the monitor 23a, and with selecting and deciding a desired one from the candidates, a combination of dichroic mirrors and various filters is finally set on the microscope.

Specifically, every time the user arbitrary sets a plurality of combinations of optical members 2-4, 12, 13, 16, 17 and 20 shown in FIG. 1, a plurality of fluorescence detection wavelength ranges corresponding to respective combinations are shown on the monitor 23a as selection candidates, and the combinations are stored in the memory of the PC 23. Although two candidates are listed in FIG. 12, the candidates may be three or more. The number of candidates displayed on the monitor 23a is determined by the combination of optical members (which is set by the user). Then, the user finally selects a desired combination of filters among candidates of fluorescence detection wavelength ranges shown on the monitor 23a, and by placing a check in the check space "☐" on the monitor 23a, the selection of the candidate is completed.

Accordingly, the user can select a combination of optical members (barrier filters, excitation filters, dichroic mirrors, and the like) having the optimum fluorescence detection wavelength range suitable for an experiment among various candidates of fluorescence detection wavelength range.

Figure 13:
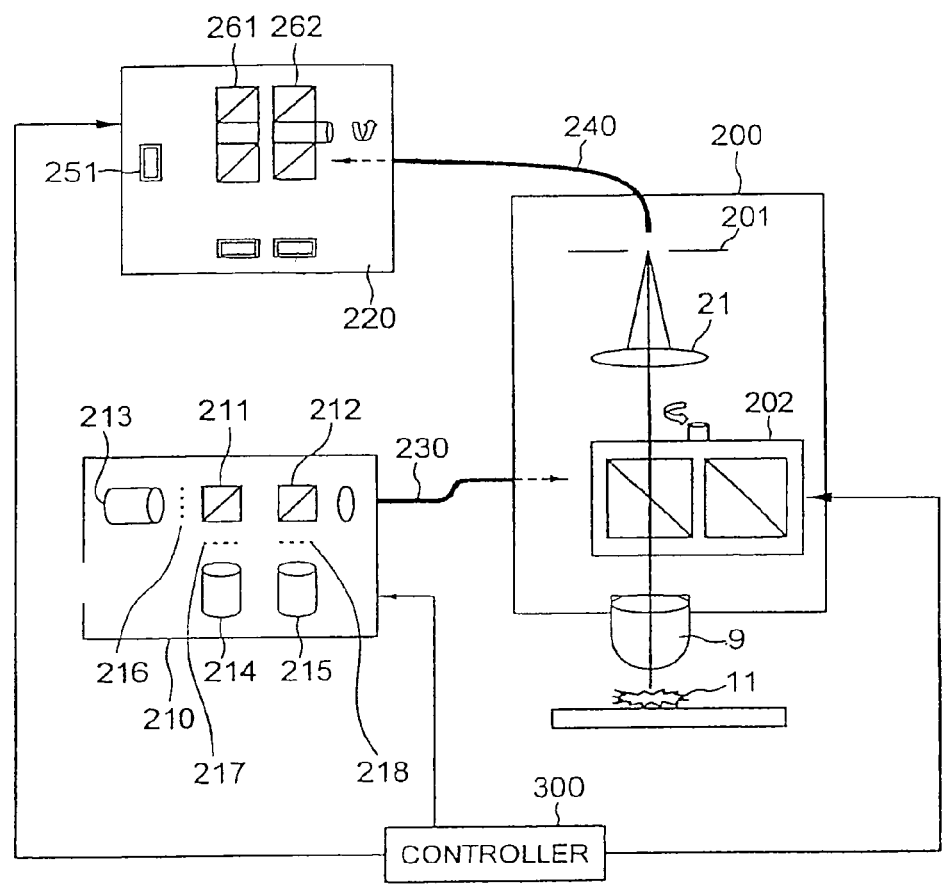
FIG. 13 is a schematic diagram showing a confocal microscope according to the embodiment.

Then, a confocal microscope according to the present embodiment is explained. FIG. 13 is a schematic diagram showing a confocal microscope according to the embodiment.

In FIG. 13, the confocal microscope is composed of a microscope body 200, a laser light source unit 210 and a sensor unit 220. The microscope body 200 is equipped with a pinhole 201, and a dichroic mirror turret 202, which is an optical member and includes a plurality of dichroic mirrors having different wavelength characteristics with each other. The laser light source unit 210 is equipped with laser light sources 213 through 215 having three different excitation light sources, shutters 216 through 218 disposed in front of each laser light source for blocking/opening laser light, and excitation filters 211 and 212 which are optical members. The sensor unit 220 is equipped with filter blocks 261 and 262 each of which has a plurality of filter cubes having different wavelength characteristics composed of a dichroic mirror and a barrier filter. The microscope body 200, the laser light source unit 210 and the sensor unit 220 are optically connected by optical fibers 230 and 240.

These optical members are disposed on the turret, and driven by a motor or manually, and a desired one can be selected. Similarly, in order to select excitation filters 211 and 212, one of shutters 216 through 218 is opened, and the others are closed. Similar to the above-described FIG. 1, spectral transmittance data of the optical members are stored in the memory of the controller 300, and the selection of these optical members (including the selection of shutters 216 through 218) is controlled by the controller 300, so that setting of optical members is electrically controlled.

Accordingly, similar to the above-described FIG. 12, candidates of fluorescence detection wavelength range are displayed on the monitor 23*a*, and when the user selects a desired candidate, the controller 300 sets the optimum optical members.

As described above, in the present confocal microscope, although optical members having various wavelength characteristics are complicatedly disposed, with composing them according to the present invention, desired fluorescence detection wavelength range can quickly be set. In the PMT (sensor) 251, since light reaching to the sensor may be affected by the wavelength characteristics of the disposed optical members according to circumstances, gain adjustment (including exposure time adjustment) is carried out by just that much by the controller 300.

A display according to the present embodiment can be used not only for the above-described laser fluorescence microscope but also for various kinds of fluorescence microscope such as an epi-illumination fluorescence microscope, a transmission fluorescence microscope, a confocal fluorescence microscope, a confocal scanning fluorescence microscope, and the like.

What is claimed is:

1. A fluorescence microscope comprising:
an illumination optical system that illuminates a sample with excitation light;
a fluorescence detection optical system that detects fluorescence from the sample;
optical members disposed on an optical path of the illumination optical system or on an optical path of the fluorescence detection optical system, at least two of the optical members having different wavelength characteristics with each other, and included in the illumination optical system or in the fluorescence detection optical system; and
a display that displays wavelength characteristics combined by calculating each wavelength characteristic of a plurality of selected optical members on a frame.

2. The fluorescence microscope according to claim 1, wherein the display displays each wavelength characteristic of fluorescent dye emanating said fluorescence on the same frame with the combined wavelength characteristics of said selected optical members.

3. The fluorescence microscope according to claim 1, further comprising:
the optical members, at least two thereof having different wavelength characteristics with each other, being exchangeably disposed on the optical paths;
an optical member detection means that detects the optical members disposed on the optical paths; and
a controller that displays on the display wavelength characteristic combined by calculating each of the wavelength characteristics of the optical members detected by the optical member detection means.

4. The fluorescence microscope according to claim 3, wherein the controller compares detectable fluorescence detection wavelength range of fluorescent dye derived from combining by calculating each wavelength characteristic of the detected plurality of the optical members with fluorescent wavelength of the fluorescent dye added in the sample, and displays a warning on the display when the fluorescent wavelength of the added fluorescent dye does not come within the fluorescence detection wavelength range.

5. The fluorescence microscope according to claim 1, wherein the optical members include a dichroic mirror.

6. The fluorescence microscope according to claim 1, wherein the optical members include an absorption filter or a barrier filter.

7. The fluorescence microscope according to claim 1, further comprising: a controller that selects one of the plurality of optical members and sets it on the optical path of the illumination optical system or the fluorescence detection optical system; wherein the display displays a plurality of candidates of the fluorescence detection wavelength range, one of which can be selected, and makes the controller carry out setting an optical member according to the selected candidate.

* * * * *

UNITED STATES PATENT AND TRADEMARK OFFICE
CERTIFICATE OF CORRECTION

| | | |
|---|---|---|
| PATENT NO. | : 8,451,533 B2 | Page 1 of 1 |
| APPLICATION NO. | : 12/801222 | |
| DATED | : May 28, 2013 | |
| INVENTOR(S) | : Yutaka Sasaki | |

It is certified that error appears in the above-identified patent and that said Letters Patent is hereby corrected as shown below:

On the Title Page Col. 1 Item (63) (Related U.S. Application Data), Line 1, Delete "PCT/JP2007/071485," and insert -- PCT/JP2008/071485, --, therefor.

In the Specification

Column 1, Line 4, Delete "PCT7JP2008/0714B5," and insert -- PCT/JP2008/071485, --, therefor.

Column 1, Line 7, Delete "bv" and insert -- by --, therefor.

Signed and Sealed this
Twenty-fourth Day of September, 2013

Teresa Stanek Rea
*Deputy Director of the United States Patent and Trademark Office*